United States Patent [19]

Whiteside et al.

[11] Patent Number: 4,935,023

[45] Date of Patent: Jun. 19, 1990

[54] FEMORAL SURFACE SHAPING GUIDE FOR KNEE IMPLANTS

[75] Inventors: Leo A. Whiteside, Bridgeton, Mo.; Carl M. Stamp, Cordova, Tenn.

[73] Assignee: Dow Corning Wright, Arlington, Tenn.

[21] Appl. No.: 294,841

[22] Filed: Jan. 9, 1989

[51] Int. Cl.[5] ............................................. A61B 17/00
[52] U.S. Cl. ........................................ 606/88; 606/80
[58] Field of Search ......... 623/20; 128/92 V, 92 VD, 128/92 VW, 92 VY; 33/227, 233; 606/62, 80, 87–89

[56] References Cited

U.S. PATENT DOCUMENTS

| | | | |
|---|---|---|---|
| 2,268,758 | 1/1942 | Martin | 33/227 |
| 3,698,091 | 10/1972 | Merrill et al. | 33/233 |
| 4,487,203 | 12/1984 | Androphy | 128/92 VW X |
| 4,722,330 | 2/1988 | Russell et al. | 606/88 |
| 4,736,737 | 4/1988 | Fargie et al. | 606/88 |

FOREIGN PATENT DOCUMENTS 0243109  10/1987  European Pat. Off. ....... 128/92 VY

OTHER PUBLICATIONS

Microloc Total Knee System, a Brochure by Johnson and Johnson Products Inc., Orthopaedic Division, 2 pages, 8-1985.

Primary Examiner—Richard J. Apley
Assistant Examiner—David F. Crosby
Attorney, Agent, or Firm—Allan O. Maki; Howard W. Hermann

[57] ABSTRACT

The present invention relates to a distal femoral surface shaping guide for mounting on an intramedullary alignment which references the central long axis of the femur in shaping the distal femoral surface and a method for shaping the distal femur using that shaping guide with particular applicability for shaping one condyle for attachment of a unicondylar prosthesis. The alignment guide of the present invention is adjustable relative to the surface of the condyle to insure that the distal femoral condyle is resected relative to that surface. The alignment guide of the present invention utilizes visual sighting studs and provides a main body which remains attached to the intramedullary alignment guide throughout the entire shaping of the distal femur.

9 Claims, 2 Drawing Sheets

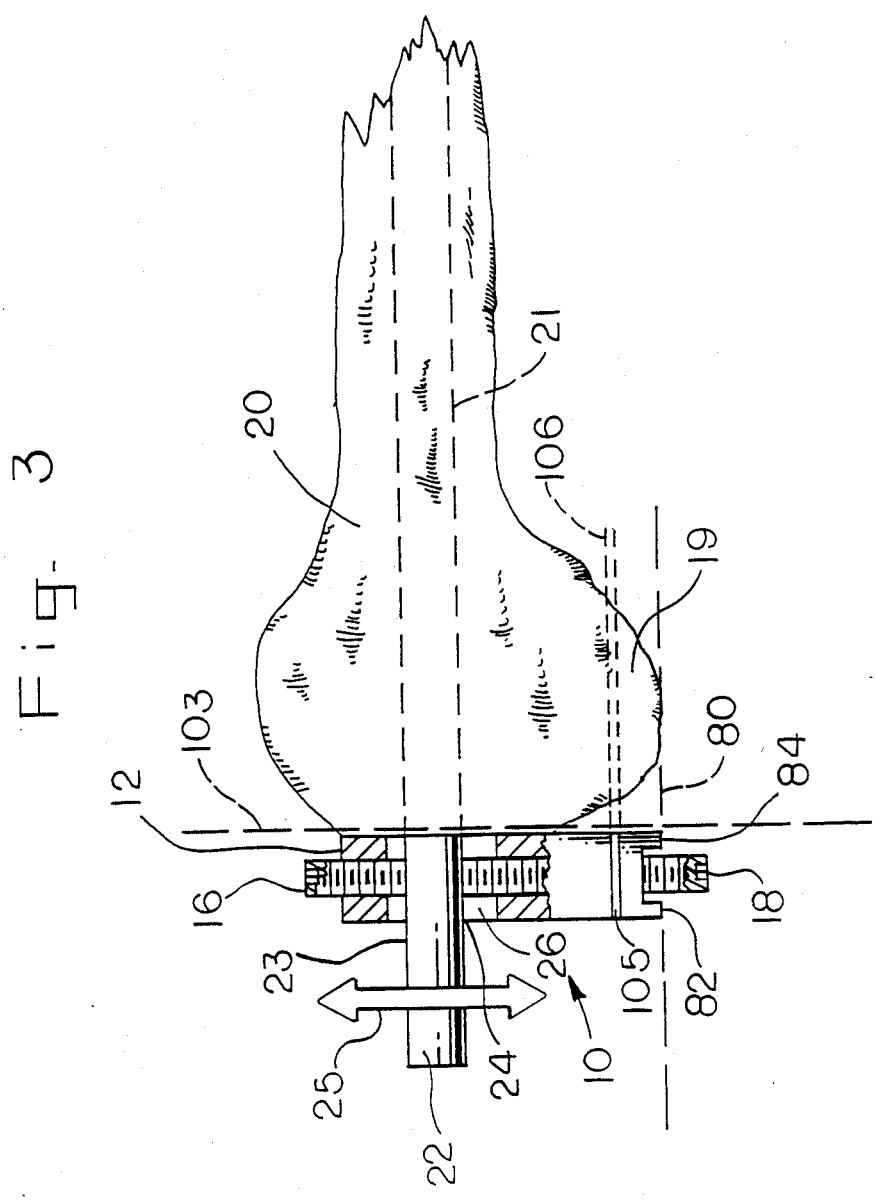

FEMORAL SURFACE SHAPING GUIDE FOR KNEE IMPLANTS

BACKGROUND OF THE INVENTION

This invention relates to a method and apparatus for shaping the distal surfaces of a human femur, employing a novel adjustable shaping guide, which is fixed to an intramedullary alignment guide which aligns with the central long axis of the femur. The invention has particular applicability to surgery in which only a single condyle, either the medial or lateral condyle, is replaced with a unicondylar prosthesis.

In replacing a knee joint which has been damaged due to disease or trauma, it is very important that the prosthesis used to replace the damaged portion of the joint be properly aligned with respect to the bone to which the prosthesis is fixed. Particular problems are encountered when replacement of only one condyle with a unicondylar prosthesis is required, in that most femoral shaping instrumentation relys on aligning with respect to the cortical aspect of the anterior condyle whereas in most replacements of only a single condyle it is the distal and posterior condyles that should be referenced for alignment. Alignment using the unaffected side of the femur as a reference point does not facilitate ease and accuracy in aligning such prostheses. This difficulty is due to the poor visability of the unaffected posterior condyle resulting from soft tissue obstruction and limited surgical exposure.

To enable a surgeon to shape the distal femur to receive a femoral component of a total knee joint prosthesis, Leo A. Whiteside, one of the named inventors herein, developed a method and apparatus for shaping a distal femoral surface which is claimed in U.S. Pat. No. 4,474,177 (issued 10/2/1984). That '177 Patent is hereby incorporated by reference to teach the use of an intramedullary alignment guide which provides the surgeon with a means for determining the central long axis of the femur and a means by which the surgeon can shape the distal femur relative to that axis by attaching distal femoral shaping instruments to that alignment guide. The '177 Patent teaches the use of a number of shaping guides to accomplish the shaping of the distal femoral surfaces. A more detailed surgical procedure describing this method of shaping the distal femur is described in Brochure No. L095-0201 9/85 entitled "Whiteside ORTHOLOC (TM) Total Knee System" from Dow Corning Wright, Arlington, Tenn. (1985). Specific examples of two such shaping guide instruments described in that brochure (A/P Bevel Cutting Guide and Distal Cutting Guide) are shown in Brochure No. L095-PN003 entitled "New Whiteside ORTHOLOC (TM) Total Knee Instruments" also by Dow Corning Wright. This type of cutting guide may be used in conjuction with the guide of the present invention to obtain correct rotational alignment and for distal condyle resection immediately prior to use of the guide of this invention.

The shaping guide instruments described in the above patent and brochure lock onto the handle of the alignment guide and take their alignment from the position of the alignment guide handle. The distal cutting guide disclosed in the last mentioned brochure includes a sighting bar for rotational alignment. The purpose of this bar is to assure that the intramedullary rod is positioned in the proper rotational alignment for the particular knee being worked on. Brochure No. 86-038-5780-0525/16MA (1986) from Zimmer, Inc., Warsaw, Ind., entitled "ZIMMER (R) Intramedullary Knee Instrumentation For the Miller Galante Total Knee System" shows an Anterior Femoral Cutting Guide Instrument No. 5785-018 which uses a locator to reference the anterior femoral cortical surface and thus guide resection of the anterior aspects of the femoral condyles relative to that anterior cortical surface. That Guide Instrument is mounted on a Femoral IM (intramedullary) Alignment Guide No. 5785-012. However, the other distal femoral surfaces are then shaped after the IM Alignment Guide is removed from the femur and several different shaping guides are employed to accomplish the shaping of the femur.

U.S. Pat. No. 4,722,330 issued to Russell and Whiteside teaches the use of a feeler gauge which references the anterior femoral cortical surface to locate a femoral surface shaping guide which is similarly mounted on an intramedullary rod.

SUMMARY OF THE INVENTION

It is a primary object of this invention to provide a method and means for aligning a shaping guide which overcomes the problems heretofore experienced in connection with instrumentation for implantation of a unicondylar femoral prosthesis. The method and apparatus of this invention provide for simple, but accurate shaping guide alignment. Another object of the present invention is to provide a simple method and apparatus for shaping the posterior and posterior bevel aspects of one condyle of the distal femur to receive a unicondylar femoral prosthesis using a distal femoral shaping guide which is designed to be fixed to support means present on (e.g., the handle of) an intramedullary alignment guide so that shaping can be done relative to the central long axis of the femur. A principal object is to provide an improved means for alignment of the guide in the anterior/posterior direction, providing a surgeon with a shaping guide which has a main body that is attached and aligned easily during the surgical procedure. It is another object of the present invention to provide a shaping guide which is adjustable anteriorly/posteriorly and which provides for alignment with respect to the posterior femoral condylar surface to permit accurate shaping of the posterior aspect of one distal femoral condyle. Such alignment coupled with attachment to a rod located along the central long axis of the femur provides points of reference for all shaping operations.

The shaping guide of the present invention is adjustable with respect to the handle of the alignment guide so that a posterior femoral condylar sighting guide which is fixed to the surface of the main body comprising the shaping guide can be used to direct raising or lowering of the cutting guide surfaces. This permits the posterior and posterior bevel aspects of the femoral condyle to be shaped relative to the edge of the posterior femoral condylar surface. The main body of the shaping guide, which attaches to the handle of the alignment guide, remains fixed to the handle after the main body is adjusted relative to the posterior femoral condyle. Preferably, the main body contains at least one shaping guide surface formed as a part of the main body. It is preferred that the main body contain integrally formed shaping guide surfaces for shaping the anterior or posterior aspects of one of the distal femoral condyles and, more preferably, further contain bevel cutting guide surfaces. Preferably the body of the guide also is reversible so that it may be used alternately to shape either a medial or lateral condyle.

With the exception of the distal femoral saw guide, the main body contains all shaping guide surfaces required to complete the shaping of one femoral condyle, formed as an integral part of the main body and no further shaping guides need be attached to the main body during the process of shaping the distal femur.

BRIEF DESCRIPTION OF THE DRAWINGS

The above and other objects, features, and advantages of the present invention will become apparent to those skilled in the art upon an examination of the following description and drawings which are illustrative of the present invention.

In the Drawings:

FIG. 3 is a side perspective view showing intramedullary alignment guide 21 inserted into the intramedullary canal of femur 20 using main body 12 (with parts broken away) as an alignment guide.

DETAILED DESCRIPTION OF THE INVENTION

Figure 1:
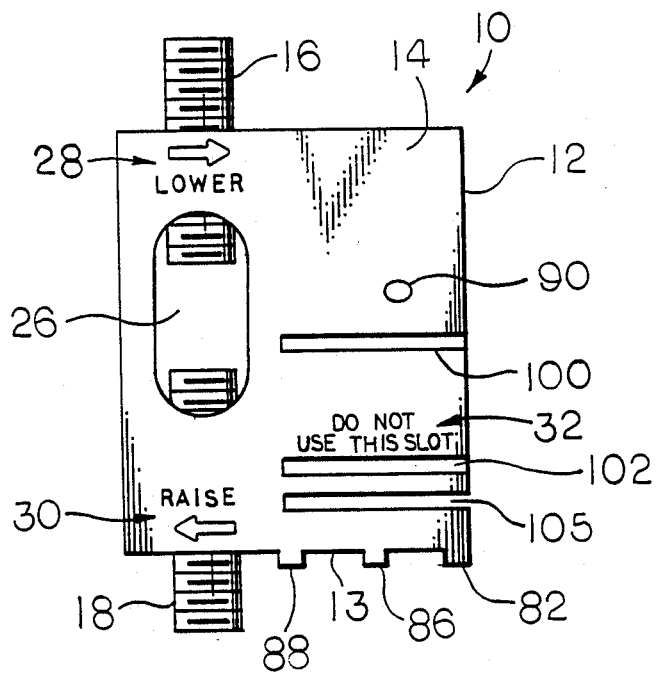
FIG. 1 is a front view of main body 12 of the femoral shaping guide 10 of the present invention.
Figure 2:
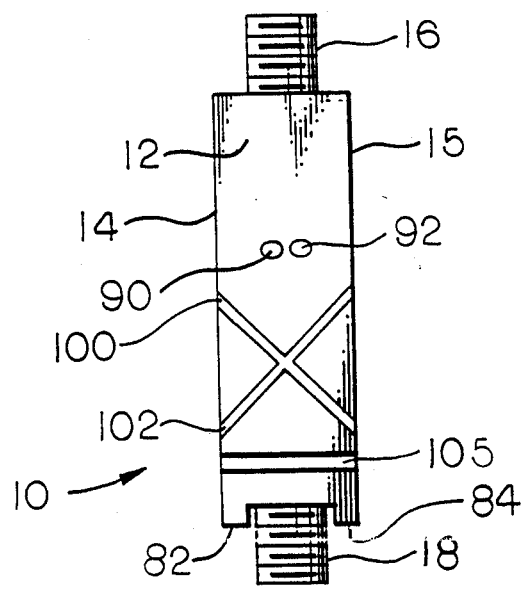
FIG. 2 is a right side view of FIG. 1.

Referring to the Drawings, the preferred embodiment of the apparatus of the present invention is shown as unicondylar distal femoral condyle shaping guide 10 composed of main body 12 having upper surface 14 which faces outwardly when guide 10 is used in cutting the lateral aspect of the left femur 20 or the medial aspect of the right femur. The opposite surface 15 is positioned outwardly for cutting of the medial aspect of the left femur or the lateral aspect of the right femur. Guide 10 is adjustably fixed to handle 22 of intramedullary alignment guide 21 as shown in FIG. 3 using opposed threaded screws 16 and 18 which are seated in threaded bores in body 12 and which serve to grasp planar surfaces 23 and 24 of handle 22. Screws 16 and 18 may be provided with a socket to receive an Allen hexagonal wrench or similar device of conventional design. Arrows 25 graphically show the adjustability of the shaping guide 10 relative to the long axis of femur 20. Opening 26 in body 12 permits a view of the ends of the set screws 16 and 18 which engage handle 22. Instruction marks indicated at 28, 30 and 32 are inscribed on each face 14 and 15 of main body 12 to better enable a surgeon to work with the cutting guide. While English language inscriptions are indicated, such inscriptions can, of course, be made in any other desired language.

Preferably main body 12 contains two sets of shaping means guide surfaces formed as a part of the main body. Thus, main body 12 contains posterior condyle shaping means guide surface 105 and bevel condyle shaping means guide surface 100. Guide means 102 is provided in order to make main body 12 reversible, and thus usable for shaping a condyle on the opposite side of the femur from that shown in FIG. 3. Line 103 represents a plane along which the distal femur has been resected just prior to use of the cutting guide of this invention. As noted above, the guide of the Whiteside '177 patent may be used in guiding such resection.

Line 106 represents the intended line along which the posterior condyle is to be cut. Line 106 is parallel to line 80 which is colinear with the lower edges of sighting studs 82 and 84. Each pair of sighting studs forms a sighting guide or gauge which enables the surgeon to visually align the cutting guide 10 in proper position relative to the posterior femoral condyle. Alternate pairs of sighting studs 86 and 88 are provided to provide some latitude to the surgeon in sighting the edge of the posterior condyle. Each pair of raised sighting studs has its free ends aligned in a direction parallel to the intramedullary alignment rod. The cutting guides 100, 102 and 105 are selected to receive a shaping instrument such as an oscillating saw blade. The spacing between lines 80 and 106 is selected to suit the amount of distal femoral condyle surface necessary to be removed to properly fit a femoral component of a unicondylar knee prosthesis on femur 20. If desired, but less preferable, separate guides for shaping, for example, the bevel and posterior (or anterior) aspects of the distal femoral condyles could also be employed.

The above described main body, intramedullary alignment guide, shaping means guide, and associated components are all preferably manufactured from a suitable surgical grade of stainless steel or other metal commonly employed by those skilled in the art to construct surgical tools for use in contact with the body. The exact composition of the materials used to construct the above forms no part of the present invention as long as it performs the desired function; other materials suitable for use within the body and for the intended uses of the above may be used without altering the nature of the invention.

The manner in which the apparatus of the present invention may be used will now be described. The present invention relies on the use of an intramedullary alignment guide to reference the shaping of the distal femur to the central long axis of the femur as defined by that intramedullary alignment guide. The preferred intramedullary alignment guide employed in conjunction with the present invention is that described in the Whiteside '177 Patent which has been incorporated by reference herein and the manner in which that intramedullary alignment guide is used is further described in the Dow Corning Wright brochures noted above. While the type of intramedullary alignment guide and manner of placing it within the intramedullary canal preferred is that of the Whiteside '177 Patent type, other intramedullary alignment guides can be employed with the shaping guide of the present invention provided that the shaping guide of the present invention can be attached to such an alternative alignment guide in such a way as to permit shaping of the distal femoral surface relative to the central long axis of the femur as defined by the alignment guide. The intramedullary alignment guide may be inserted within the femur using various guides to direct the surgeon as to where to place the boring tool used to create a passage for the intramedullary alignment guide. The type of intramedullary alignment guide employed and the manner in which it is placed within the femur is conventional and forms no part of the present invention.

FIG. 3 shows intramedullary alignment guide 21 of the same type which is described in the Whiteside '177 patent being placed within a bore in femur 20 running through the intramedullary canal. The bore has been prepared in accordance with the Whiteside method such that central long the axis of the intramedullary rod 21 is concentric with the central long axis of femur 0 after the rod has been inserted to its full length (i.e., approximately up to the point where Guide 21 is selected such that handle 22 is set at an angle relative to the central axis of femur 20 to provide the desired degree of valgus angle the surgeon wishes to obtain on the knee prosthesis after implantation.

The intramedullary alignment guide 21 has been inserted within the bore in femur 20 up to the point where fins (not shown) almost touch the distal surface of femur 20. The rotational alignment of guide 82 is adjusted using the Whiteside method and guide 21 is then driven into the femur using a mallet on the impactor until the fins are embedded in the cortical bone of the distal femur. Previous to use of the cutting guide of this invention, resection of the distal femur has been performed using, for example, the guide and surgical procedure set forth in the above noted Whiteside '177 patent. The method of the present invention is then begun.

Main body 12 has been fixed to handle 22 by tightening bolts 16 and 18 down over flat surfaces 23 and 24 of handle 22. With guide 10 locked on handle 20 as described the sight 82, 86 or 88 together with the its corresponding rear sight (of which only rear sight 84 can be seen in the drawings) is used to position the cutting guide 10 in the correct position with relation to the posterior limit of condyle 19. The surgeon can observe the sighting studs in relation to the condyle in making this alignment. Thereafter the surgeon is able to shape the condyle in accordance with conventional surgical procedures using the cutting guides provided in main body 12.

This procedure provides this method with an advance over the Whiteside '177 Patent in that the femur can be shaped relative to the surface of the posterior femoral as well as with respect to the central long axis of the femur. A second advantage over Whiteside '177 is that this invention eliminates the need to make reference to the unaffected condyle and the difficulties associated with such a procedure in the case of unicondylar replacements. A further advantage is that other alignment guides which fix to the end of the distal femur via pins driven within the bone can disrupt the integrity of the bone, particularly where the bone is osteoporotic and already weak in structure as is often the case with older patients.

After aligning main body 12 relative to the posterior condyle of distal femur 20, a conventional shaping means such as an oscillating saw or a hand saw (not shown) is then introduced into guide slot 105 to enable the surgeon to resect the distal condyle accurately along the plane indicated by line 106. In similar fashion guide slot 100 is used to cut a bevel surface. The cuts are designed to fit the particular prosthesis to be fixed to the distal femur. The prosthesis is affixed to the distal femur in conventional fashion using appropriate pins, posts or fins, which may be integral with the prosthesis, depending on the particular design. The surgeon can cut such holes or slots as are deemed desirable for securing a particular prosthesis. Appropriate slots or holes can be provided in main body 12 to assist in such cutting procedures. When shaping is completed, the intramedullary alignment guide is removed along with main body 12. Main body 12 has remained attached to the alignment guide during the entire posterior and posterior bevel shaping procedure thus maintaining its original alignment throughout the entire procedure.

As noted, guide 10 can be reversed if it is desired to shape in the same manner the opposite side of the femur using the same guide 10. Guide 10 can be used to shape the distal femur to receive a number of different femoral components simply by selecting appropriately oriented guide surfaces in the main body and/or guides which are capable of being attached to the main body. Pin holes 90 and 92 can, for example, be provided for the surgeon's use in further securing the cutting guide to the femur, if desired, but such additional anchorage is optional with the individual surgeon and not necessary to the practice of the invention.

Other modifications of the apparatus and method of the present invention will become apparent to those skilled in the art from an examination of the above specification and drawings. Therefore, other variations of the present invention may be made which fall within the scope of the following Claims even though such variations were not specifically discussed above.

That which is claimed is:

1. A distal femoral surface shaping guide for fixation to an intramedullary alignment guide having an intramedullary alignment rod portion which is fixed within the intramedullary canal of a femur in such a manner as to have the central long axis of the rod concentric with the central long axis of said femur comprising,
   (A) a main body having an upper surface facing distally with respect to the distal femur when the main body is fixed to the alignment guide, means for adjustably fixing said main body in proper alignment with respect to the central long axis of the intramedullary rod portion,
   (B) a distal femoral condylar surface sighting gauge having at least two raised sighting studs having their ends aligned in a direction parallel to said intramedullary alignment rod for visually aligning the cutting guide with respect to the outer surface of a distal femoral condyle and
   (C) at least one distal femoral surface shaping guide having shaping means guide surfaces thereon which guide cooperatively engages said attachment means to permit at least one shaping step in the resection of the distal femur in such a manner that a preselected unicondylar femoral knee prosthesis can be attached to the shaped distal femur, said main body remaining fixed to the intramedullary alignment guide during the shaping process.

2. The distal femoral surface shaping guide as claimed in claim 1 wherein the main body further contains at least one shaping means guide surface formed as a part of said main body.

3. The distal femoral surface shaping guide as claimed in claim 2 wherein the main body contains shaping means guide surfaces for shaping at least one aspect of the distal femoral condyles.

4. The distal femoral surface shaping guide as claimed in claim 3 wherein the main body further contains at least one bevel shaping means guide surfaces situated at an appropriate angle with respect to a flattened shaped distal femoral surface such that a portion of the anterior or posterior aspects of the distal femoral surface can be shaped to produce a suitably bevelled distal femoral surface.

5. The distal femoral surface shaping guide as claimed in claim 1 wherein said attachment means comprises a pair of threaded set screws which engage opposite flattened sides of said intramedullary rod.

6. A shaping guide according to claim 1 wherein additional shaping guide surfaces are provided to guide shaping of the same aspect of the opposite femur when the guide is reversed on the rod.

7. A distal femoral surface shaping guide for fixation to an intramedullary alignment guide having (a) an intramedullary alignment rod portion which is fixed within the intramedullary canal of a femur in such a manner as to have the central long axis of the rod concentric with the central long axis of said femur and (b) an external support means attached to said rod portion in an aligning relationship with respect to the central long axis of the rod portion, said shaping guide comprising, in combination,
- (A) a main body having an upper surface facing distally with respect to the distal femur when the main body is fixed to the alignment guide, a plurality of femoral surface shaping guide surfaces formed as a part of the main body, an adjustable means for fixing said main body in proper alignment with respect to the central long axis of the intramedullary rod portion, and an attachment means fixed to said main body, and
- (B) at least one pair of raised sighting studs aligned in coplanar alignment with said intramedullary alignment rod and adapted to act as a visual guide for aligning a shaping means guide surface for shaping the distal aspect of the femoral condyles by alignment of said sighting studs with a surface of the femoral condyle; wherein said main body contains a sufficient number of femoral surface shaping means guide surfaces to permit shaping of the distal femur in such a manner that a preselected femoral knee prosthesis can be attached to the shaped distal femur, said main body remaining fixed to the intramedullary alignment guide during the posterior and posterior bevel shaping processes.

8. A method of preparing one condyle of a human femur having a distal femoral surface containing medial and lateral condyles and an intramedullary canal located at the center of a tubular shaft of hard compact bone, said femur having fixed therein an intramedullary alignment guide having (a) an intramedullary alignment rod portion which is fixed within the intramedullary canal of the femur in such a manner as to have the central long axis of the rod concentric with the central long axis of said femur said method comprising the steps of attaching to said rod a shaping guide comprising main body having an upper surface facing distally with respect to the distal femur when the main body is fixed to the alignment guide, an adjustable means for fixing said main body in proper alignment with respect to the central long axis of the intramedullary rod portion, visual alignment means for aligning the main body with respect to the distal femur, and an adjustable attachment means fixing said main body to said rod, said main body optionally containing at least one femoral surface shaping means guide surface formed as an integral part of the main body,
- (II) aligning said alignment guide visually with the posterior surface of said condyle, by visually aligning said studs and the surface of said condyle,
- (III) adjusting said adjustable means to bring said main body in proper alignment with respect to the surface of the distal femoral condyle,
- (IV) modifying said distal femur through the use of one of the distal femoral surface shaping means guide surfaces present as a part of said main body,
- (V) modifying said distal femur using a distal femoral surface shaping guide having shaping means guide surfaces thereon which guide cooperatively engages said attachment means,
- (VI) repeating steps (IV) and (V) as needed until an appropriately shaped distal femoral surface is obtained, and lastly,
- (VII) removing said main body and intramedullary alignment guide from the shaped femur, wherein said main body remains fixed to the intramedullary alignment guide during the entire shaping process.

9. The method as claimed in claim 8 wherein all distal femoral surface shaping means guide surfaces necessary to accomplish complete shaping of said distal femur are formed as an integral part of the main body.

* * * * *